(12) United States Patent
Thong

(10) Patent No.: US 7,016,728 B2
(45) Date of Patent: Mar. 21, 2006

(54) ATRIAL CARDIAC PACEMAKER

(75) Inventor: Tran Thong, Portland, OR (US)

(73) Assignee: Biotronik Mess-und Therapiegeraete GmbH & Co., Berlin (DE)

( * ) Notice: Subject to any disclaimer, the term of this patent is extended or adjusted under 35 U.S.C. 154(b) by 577 days.

(21) Appl. No.: 10/330,681

(22) Filed: Dec. 27, 2002

(65) Prior Publication Data

US 2003/0167076 A1    Sep. 4, 2003

Related U.S. Application Data

(60) Provisional application No. 60/345,095, filed on Jan. 4, 2002.

(30) Foreign Application Priority Data

May 21, 2002    (DE) ................................ 102 23 243

(51) Int. Cl.
    *A61N 1/362* (2006.01)
(52) U.S. Cl. ......................................................... 607/5
(58) Field of Classification Search ............... 607/4–28
    See application file for complete search history.

(56) References Cited

U.S. PATENT DOCUMENTS

| 5,630,834 A | 5/1997 | Bardy |
| 5,919,209 A | 7/1999 | Schouten |
| 5,951,593 A | 9/1999 | Lu et al. |
| 6,058,328 A | 5/2000 | Levine et al. |
| 2002/0003160 A1 | 6/2001 | Meyer |

FOREIGN PATENT DOCUMENTS

DE    199 58 735 A1    6/2001

*Primary Examiner*—Scott M. Getzow
(74) *Attorney, Agent, or Firm*—Hahn Loeser & Parks LLP

(57) ABSTRACT

The invention concerns a pacemaker (52) designed for emitting stimulation impulses to an atrium (20) of a heart (22), with a connection for an atrial electrode wire (14) for emitting electrical impulses to the atrium (20), with an atrial stimulation impulse generator (24) that can be connected to the electrode wire (14) and is designed to generate atrial stimulation impulses that are to be emitted over an electrode wire, with a control unit (38) that is connected to the atrial stimulation impulse generator (24) and designed to trigger the stimulation impulse generator (24) in order to generate and emit atrial stimulation impulses, wherein the control unit (38) is designed in an AF-prevention mode that triggers the stimulation impulse generator (24) in order to generate a stimulation impulse sequence that is suitable for preventing atrial fibrillation (AF). It is characterized by an interval timer (34) that is connected to the control unit (32) and designed to turn the AF-prevention mode on and off according to the time of day and thereby activate or deactivate, in a time-controlled manner, the generation and emission of the stimulation impulse sequences preventing atrial fibrillation.

18 Claims, 3 Drawing Sheets

ATRIAL CARDIAC PACEMAKER

This application claims the benefit of U.S. Provisional Application No. 60/345,095 filing date Jan. 4, 2002

The invention concerns a pacemaker that is designed to emit stimulation impulses to an atrium of a heart.

Such a pacemaker normally contains a connection for at least one atrial electrode wire with which electrical impulses can be emitted to an atrium of a heart and discharged into the cardiac tissue (myocardium) in the atrium. The connection for the atrial electrode wire is usually connected to an atrial stimulation generator, which is designed in such a way that it can be triggered to generate atrial stimulation impulses that are to be emitted by the atrial electrode wire. For triggering the stimulation impulse generator, an (atrial) control unit is provided that is connected to the atrial stimulation generator and designed to trigger the stimulation generator, in order to generate and emit atrial stimulation impulses. In the case interesting here, the control unit has an AF-prevention mode in which the atrial control unit triggers the stimulation generator, in order to create a stimulation sequence that is suitable for preventing atrial fibrillation.

BACKGROUND OF THE ART

The previously sketched pacemaker is preferably an ICD (implantable cardioverter/defibrillator) with overdrive stimulation for the preventative treatment of atrial fibrillation. Customarily, such an ICD also has a connection for a ventricular electrode wire and a stimulation impulse generator for ventricular stimulation impulses that are effective in the ventricle of a heart.

In the case of the present invention, the problem of atrial fibrillation stands at the forefront. Atrial fibrillation affects a significant portion of the older population. One distinguishes two types of atrial fibrillation, namely, vagally-transmitted atrial fibrillation and adrinergic atrial fibrillation. The first-mentioned vagally-transmitted atrial fibrillation occurs in patients who are in a relaxed state, for example, during periods of digestion following meals or during the night or early morning hours. Preliminary results of clinical studies suggest that pacemakers or fibrillators that have a mode for preventative stimulation for the purpose of controlling atrial fibrillation are capable, at least by means of the so-called overdrive pacing, of at least reducing the length of vagally-induced atrial fibrillation episodes.

The overdrive stimulation known for limiting or preventing atrial fibrillation is based on the concept of permanently stimulating the largest possible number of atrial contractions and allowing the least number of natural (spontaneous intrinsic) contractions. For this reason, during overdrive stimulation, stimulation is accomplished either with a variable or a fixed, elevated atrial rate, for example, 80 to 90 beats per minute. In the case of the adaptive, variable overdrive stimulation, atrial stimulation occurs in such a way that the atrial stimulation interval corresponds to a length of approximately 95% of a corresponding natural (intrinsic) atrial interval. An example for such an adaptive overdrive algorithm is known as the applicant's DDD+ algorithm.

Since the generation of stimulation impulses requires a great deal of energy, overdrive stimulation leads to undesirably high power consumption. This impairs the life span of the pacemaker with overdrive stimulation.

The goal of the present invention is reducing the impairment to the life span of a pacemaker in conjunction with reducing or preventing atrial fibrillation.

SUMMARY OF THE INVENTION

For this purpose, in the case of a pacemaker of the aforementioned type according to the invention, an interval timer is provided that is connected to the atrial control unit and designed to turn the AF-prevention mode on or off according to the time of day and thereby activate or deactivate the generation and emission of the stimulation impulse sequence that prevents atrial fibrillation in a time-controlled manner.

The invention is based on the knowledge that the aforementioned vagally-induced atrial fibrillations frequently occur at certain times of the day, namely, at the time when the patient is resting, for example, during a period of digestion following a meal or during the early morning hours.

The invention is also based on the knowledge that atrial fibrillations certainly affect patients, but are not necessarily fatal.

In a preferable embodiment variant, the pacemaker according to the invention contains a time storage for the time of day when the AF prevention mode is turned on or off.

Preferably, the last-mentioned pacemaker is designed to receive electrical signals from the atrium of a heart and moreover has an atrial input amplifier and a detector for atrial fibrillations connected to it. The latter is connected to the control unit. The control unit is designed in such a way that it transmits the times of day that atrial fibrillation occurs. The signal of the real-time clock and that of the atrial fibrillation detector serve as input signals for the control unit. The control unit produces turn-on times as the output signals for the AF-prevention mode and stores these times in the time storage. The control unit is thus designed in such a way that the transmitted and stored switching times correspond to the times of day when atrial fibrillations frequently occur.

The detector for atrial fibrillation (AF detector) can be connected to a p-wave detector, which is designed to detect p-waves occurring with an atrial contraction in an intracardial electrocardiogram (ECG).

The control unit is preferably—at least part of the time—connected to a statistics storage and acts together with the statistics storage in such a way that the times when atrial fibrillations occur more frequently are stored for several different days.

In a special embodiment variant, the statistics storage and a plotting unit for determining the turn-on and turn-off times are components of an external patient device that has a telemetry unit that enables a corresponding telemetry unit in the implant of a telemetric connection between the plotting unit of the patient device and the control unit of the implant. Such an arrangement with an external, telemetrically integratable patient device enables an exhaustive evaluation of data on the occurrence of atrial fibrillations without exerting stress on the implant, above all with regard to power consumption.

In regard to the last-mentioned embodiment variant, preferably, an implant is provided that has a telemetry unit that enables a telemetric connection between the implant and an external patient device, especially between the control unit of the implant and the plotting unit of the external patient device. As previously described, such an arrangement enables the determination of the turn-on/turn-off times for the AF-prevention mode that is performed by the plotting unit in the patient device—also aided by complex algorithms. These turn-on/turn-off times are then transmitted by a telemetric connection from the patient device to the implant and stored there in the time storage.

Preferably, the time storage is designed to store an n-Bit-long signal and acts together with the control unit in such a way that each bit of the signal is allocated a predetermined time period and that the status of a respective signal bit (0 or 1) indicates whether the AF-prevention mode is turned on or off for the time allocated the respective bit. Especially suitable for this is a 48-bit memory in which each of the 48 bits stands for a defined half-hour time period.

In the case of this kind of particularly simple embodiment, the real-time clock signal can be a simple address signal for the 48-bit memory. The respective bit (0 or 1) is read out of the memory and delivered to the atrial control unit. When Bit 1 is read out, the AF-prevention mode of the atrial control unit is turned on; if Bit 0 is read out, the AF-prevention mode remains off. Thus, the signal status of the read out bits (0 or 1) directly turns the AF-prevention mode on or off.

In one embodiment type, the time storage must be programmed by a physician.

In an alternate embodiment variant, the time storage is designed to directly store the turn-on/turn-off times and acts together with the control unit in such a way that the AF-prevention mode is turned on at a stored turn-on time and remains turned on until the AF-prevention mode is turned off again at the next turn-off time and remains off until the next turn-on time. In this embodiment variant, a bit of a signal stored in the time storage is thus not a direct indication that the AF-prevention mode is being turned on or off at the time of day allocated to the respective bit. Rather, times are directly stored in the time storage as turn-on/turn-off times (in contrast to the bits that mark certain time periods). This type of time storage certainly requires a great deal of memory space; however, it enables turn-on/turn-off times that correspond to "irregular" time periods and, for example, deviate from a half-hour grid. This last-mentioned embodiment variant is also especially suitable for an implant with a telemetry unit. The determination of the turn-on/turn-off times then occurs analogous to the previously described manner by means of a plotting unit in one—at least partially—telemetrically connected external patient device.

Preferably, the pacemaker is designed to emit atrial stimulation impulse sequences in overdrive mode when the AF-prevention mode is switched on.

Alternatively, the pacemaker in AF-prevention mode is designed to trigger stimulation impulse sequences having an elevated atrial rate of preferably 80 to 90 impulses per minute.

BRIEF DESCRIPTION OF THE DRAWINGS

The invention should now be described in greater detail using an embodiment example. The figures show.

DETAILED DESCRIPTION OF A PREFERRED EMBODIMENT

Figure 1:
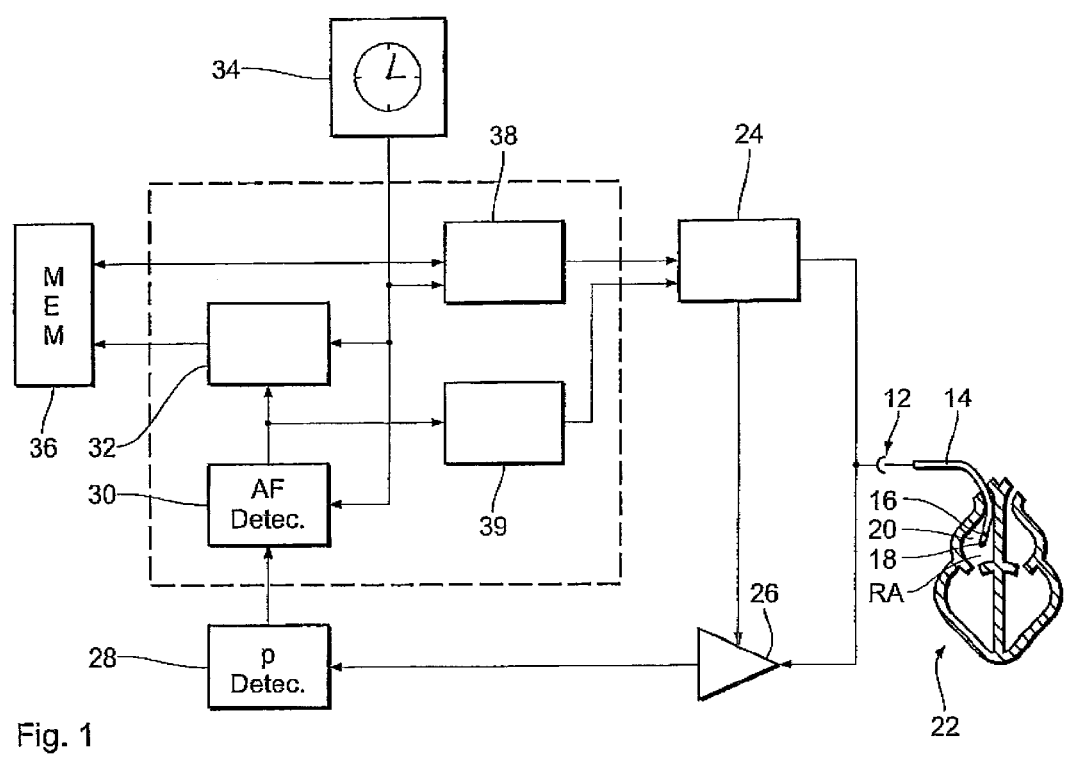
FIG. 1 a schematic block diagram of the components of a pacemaker that are of interest for the present invention FIG. 2 components of an especially simple control in a schematic block diagram FIG. 3 a block diagram of an implantable pacemaker of the type sketched in FIG. 1, including an additional telemetric unit and corresponding external patient device

In FIG. 1, only those pacemaker components that are important for the present invention are shown in a schematic drawing. These are a connection 12 for an atrial electrode wire 14 with—as shown in the embodiment example—two electrodes 16 and 18. The electrode 16 is designed as an annular electrode, and the electrode 18, as a point electrode. The distal end of the electrode wire 14 is designed to be placed in the atrium 20 of a heart 22.

The depicted components of a pacemaker comprise a stimulation impulse generator 24 for generating atrial stimulation impulses. The stimulation impulse generator 24 is moreover connected to the electrode wire 14 via the connection 12.

An input amplifier 26 is also connected to the electrode wire 14 via the connection 12. The atrial input amplifier 26 is designed to amplify electrical signals received in the atrium 20 of a heart 22 and process them for further evaluation.

On the output side, the input amplifier 26 is connected to a p-wave detector 28 that is designed to detect p-waves in the intracardial electrocardiogram, which are characteristic for a contraction of the atrium 20 and have been processed by the input amplifier 26.

The p-wave detector 28 is connected on the output side to an AF detector 30 for detecting atrial fibrillation. The AF detector 30 also determines the frequency of p-wave occurrence. This can be performed either by counting the number of p-waves that occur in a defined time period specified by the interval timer; or, alternatively, with each p-wave, an interval timer can be started that can then be stopped by the following p-wave, so that, in this manner, the interval between two p-waves can be determined. If this interval falls below (for example, 6 counting steps) a specified value, then this corresponds to an elevated atrial rate and can, for example, be assessed as an atrial fibrillation. In the case of atrial fibrillation occurrence, the AF detector 30 emits a corresponding output signal that is fed into a memory control unit 32. An output signal of a real-time clock 34 is likewise fed into this storage control unit 32. The storage control unit 32 can be designed differently in the different embodiment variants.

In a simple embodiment variant, the storage control unit 32 is designed to generate an address signal for a time storage 36 from the time signal of the real-time clock 34, in case a signal from the AF detector 30 indicating an atrial fibrillation is present. The storage control unit 32 then ensures that a bit with a status corresponding to the switch-on of the AF-prevention mode, for example, number 1, is stored under the address determined by the real-time clock.

In the case of this simple embodiment variant, an atrial stimulation control unit 38 is also connected to the real-time clock 34 and to the time storage 36 and designed in such a way that it reads out the time storage 36 at the address specified by the real-time clock 34 and, depending upon the switch status of the read out bit (0 or 1), switches an AF-prevention mode on or off. If, for example, the bit at the address of the time storage 36 that was specified by the real-time clock 34 is "1", then the stimulation control unit 38 assumes the AF-prevention mode and triggers the stimulation impulse generator 24 in such a way that this generator generates stimulation impulses having an elevated atrial rate, for example, in overdrive mode.

If the bit that the stimulation control unit 38 reads out of the time storage 36 corresponding to the time is "0", then the stimulation control unit 38 does not trigger the stimulation impulse generator 24 into AF-prevention mode. Depending upon the design of the pacemaker, the triggering of the stimulation impulse generator 24 is performed by the stimulation control unit 38 in the customary manner, i.e., atrial stimulation impulses are generated when there is no occurrence of natural atrial contractions (and, correspondingly, no p-waves detected by the p-wave detector 28) within a specified time, for example, following a ventricular event (VA time).

Figure 3:
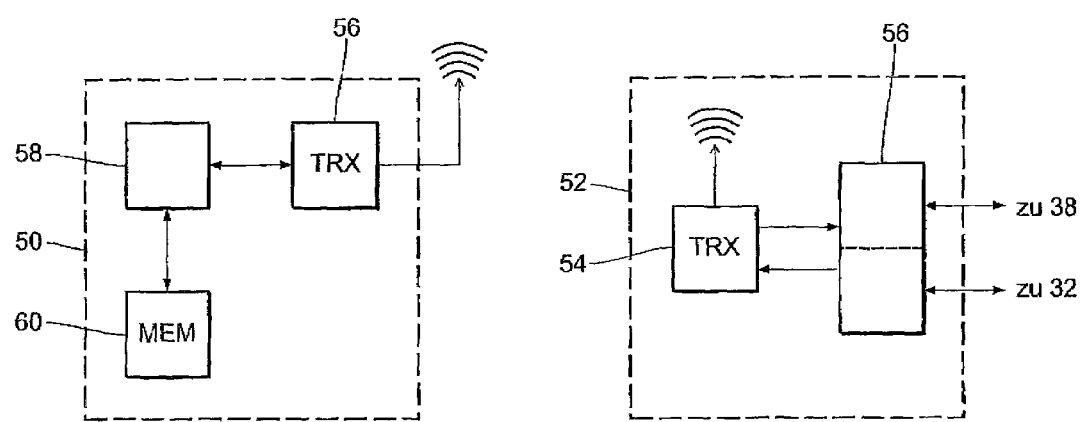

In another variant described in conjunction with FIG. 3, the storage control unit 32 is alternatively designed in such a way that the times of atrial fibrillation occurrence are stored in the time storage 36 for further evaluation by a plotting unit in an external patient device.

The time storage 36 in the last-mentioned embodiment variants is designed in two parts. In addition to storing the occurrence times of atrial fibrillation, which has already been described, the time storage 36 contains the turn-on/turn-off times for the AF-prevention mode in the second part. In the case of this embodiment variant, the stimulation control unit 38 is designed in such a way that the AF-prevention mode is activated when the time specified by the real-time clock 34 corresponds to a turn-on time stored in the second part of the time storage 36. Conversely, the AF-prevention mode is again deactivated when a time specified by the real-time clock 34 corresponds to a turn-off time stored in the second part of the time storage 36. In the simplest part, turn-on/turn-off times are stored in strictly alternating fashion in the second part, so that, with every time stored in the time storage 36, the AF-prevention mode is switched from "on" to "off" or, conversely, from "off" to "on". Then, a special bit that differentiates a turn-on time from a turn-off time does not need to be stored. In addition to the time signal, it is also possible to store a bit for each switching time that modifies the switching time as either a turn-on or turn-off time.

Only for purposes of completeness, a defibrillation control unit 39 is furthermore shown that, in the case of an atrial fibrillation, reacts to the fibrillation detector 30 and can trigger the stimulation impulse generator 24 to emit an atrial defibrilation impulse.

Figure 2:
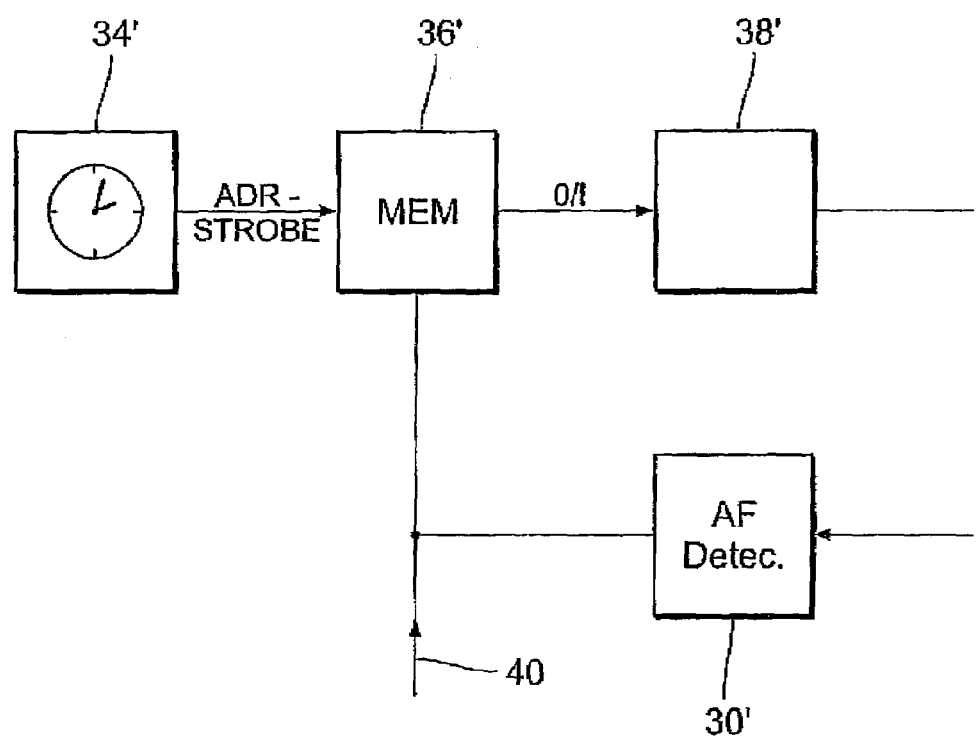

FIG. 2 is a partial depiction of a particularly simple embodiment variant, which is similar to the embodiment variant first described in connection with FIG. 1. The real-time clock 34' in this embodiment variant is designed in such a way that it directly generates an address signal for the time storage 36'. The stimulation control unit 38' must then generate only a read signal, in order to read out the time storage 36' at the storage location corresponding to the actual time. As previously described, if, for example, only a single bit is read out, then its status—either 0 or 1—directly turns the AF-prevention mode on or off.

In order to store a turn-on time in the time storage 36', only a write signal must be generated either by a physician via an external interface 40 or by the AF detector 30', in order to set the bit to the desired status at the storage location specified by the respective time, for example, "1" for turning on the AF-prevention mode.

In FIG. 3, an embodiment variant is shown in which the evaluation of the times of atrial fibrillation occurrence and the determination of turn-on/turn-off times for the AF-prevention mode are performed by an external patient device. The patient device 50 is connected to the pacemaker 52 via a telemetric connection. The pacemaker 52 basically corresponds to the one that has already been described in FIG. 1. The time storage 34" is divided into two parts. In one part of the time storage 36" (the top part of FIG. 3), the turn-on/turn-off times for the AF-prevention mode are stored. In the other part of the time storage 36" (the lower part of FIG. 3), the times of atrial fibrillation occurrence are stored. The time storage 36" is connected to a telemetric transmitted and telemetric receiver 54.

The patient device 50, which likewise leads to the telemetric sender 56, along with the telemetric transmission 54 on the implant side, enables a wireless connection between the pacemaker 52 and the patient device 50. The patient device 50 also has a plotting unit 58 that is connected to a memory 60.

In the second part of the time storage 34", the arrangement shown in FIG. 3 enables a wireless transmission of stored atrial fibrillation occurrence times to the patient device 50. In the patient device 50, these times can be stored in the storage 60 and evaluated by the potting unit 58, in order to establish the turn-on/turn-off times for the AF-prevention mode. The turn-on/turn-off times determined in this manner are transmitted from the plotting unit 58 to the first part of the time storage 34" of the pacemaker 52 by using the telemetric transmitter and telemetric receiver 54 and 56. These turn-on/turn-off times then serve to activate or deactivate the AF-prevention mode, as has already been described in relation to FIG. 1 of the second embodiment variant.

The invention claimed is:

1. A pacemaker, designed for emitting stimulation impulses to an atrium of a heart, said pacemaker comprising:
   a connection for an atrial electrode wire for emitting electrical impulses to the atrium;
   an atrial stimulation impulse generator, connectable to the atrial electrode wire and designed to generate atrial stimulation impulses that are emitted over the atrial electrode wire;
   a control unit that is connected to the atrial stimulation impulse generator and designed to trigger the atrial stimulation impulse generator in order to generate and emit atrial stimulation impulses, wherein the control unit is designed in an AF-prevention mode that triggers the stimulation impulse generator to generate a stimulation impulse sequence adapted for preventing atrial fibrillation (AF); and
   an interval timer, connected to the control unit (38) and designed to turn the AF-prevention mode on or off according to the time of day and thereby activate or deactivate, in a time-controlled manner, the generation and emission of stimulation impulse sequences preventing atrial fibrillation.

2. The pacemaker of claim 1, further comprising: a time storage for turn-on/turn-off times of the AF-prevention mode.

3. The pacemaker of claim 2, wherein: the time storage is designed to store a plurality of bits and works together with the control unit in such a way that each bit is allocated to a predetermined time period and the status of a respective bit (0 or 1) determines the activation status of the AF-prevention mode ("on" or "off") for the corresponding period of time.

4. The pacemaker of claim 3, wherein: the time storage is designed to store 48 bits and works together with the control unit in such a way that each bit is allocated to a different half-hour time period.

5. The pacemaker of claim 2, wherein: the time storage is designed to directly store turn-on/turn-off times and works together with the control unit in such a way that the AF-prevention mode is turned on at a stored turn-on time and remains on until the AF-prevention mode is turned off again at the next turn-off time and remains off until the next turn-on time.

6. The pacemaker of claim 2, further comprising: an atrial input amplifier for receiving electrical signals of the atrium; and a detector for atrial fibrillations connected to the atrial input amplifier, the detector being also connected to the control unit;

wherein the control unit is designed to determine time periods when atrial fibrillations occur through signals of the interval timer and of the atrial fibrillation detector.

7. The pacemaker of claim 6, wherein: the control unit is designed to create turn-on times for the AF-prevention mode from the time periods during which atrial fibrillations occur and store them in the time storage.

8. The pacemaker of claim 6, further comprising: a telemetric receiver that is indirectly connected to the time storage in such a way that the turn-on/turn-off times can be recorded telemetrically into the time storage.

9. The pacemaker of claim 8, wherein: the control unit is designed in the AF-prevention mode in order to trigger the generation and emission of a stimulation impulse sequence in the overdrive mode.

10. A device for use external to a patient using a pacemaker according to claim 8, comprising:

a telemetric transmitter/receiver that is linked to a plotting unit and a memory, wherein the memory is designed to store the time periods when atrial fibrillations occur and the plotting unit is designed to create the turn-on/turn-off times for the AF-prevention mode of the pacemaker from the stored time periods.

11. The patient device of claim 10, wherein: the patient device is designed to telemetrically transmit turn-on/turn-off times for the pacemaker's AF-prevention mode to the pacemaker.

12. The pacemaker of claim 6, further comprising: a telemetric transmitter that is linked to at least one of the control unit and the time storage and is designed to transmit time periods when atrial fibrillations occur to an external patient device.

13. The pacemaker of claim 12, wherein: the control unit is designed in the AF-prevention mode in order to trigger the generation and emission of a stimulation impulse sequence with an elevated atrial rate in the range of 80 to 90 impulses per minute.

14. A device for use external to a patient using a pacemaker according to claim 12, comprising:

a telemetric transmitter/receiver that is linked to a plotting unit and a memory, wherein the memory is designed to store the time periods when atrial fibrillations occur and the plotting unit is designed to create the turn-on/turn-off times for the AF-prevention mode of the pacemaker from the stored time periods.

15. The patient device of claim 14, wherein:

the patient device is designed to telemetrically transmit turn-on/turn-off times for the pacemaker's AF-prevention mode to the pacemaker.

16. The pacemaker of claim 2, further comprising:

a telemetric receiver that is indirectly connected to the time storage in such a way that the turn-on/turn-off times can be recorded telemetrically into the time storage.

17. The pacemaker of claim 1, wherein:

the control unit is designed in the AF-prevention mode in order to trigger the generation and emission of a stimulation impulse sequence with an elevated atrial rate in the range of 80 to 90 impulses per minute.

18. The pacemaker of claim 1, wherein:

the control unit is designed in the AF-prevention mode in order to trigger the generation and emission of a stimulation impulse sequence in the overdrive mode.

* * * * *